(12) United States Patent
Owens et al.

(10) Patent No.: US 6,902,571 B2
(45) Date of Patent: Jun. 7, 2005

(54) COMPACTED CATHETER BALLOON AND METHOD OF INCREMENTAL COMPACTION

(75) Inventors: Timothy Owens, Dublin, CA (US); Florencia Lim, Union City, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 68 days.

(21) Appl. No.: 10/230,432

(22) Filed: Aug. 29, 2002

(65) Prior Publication Data

US 2004/0044309 A1 Mar. 4, 2004

(51) Int. Cl.[7] .............................................. A61M 29/00
(52) U.S. Cl. ................................. 606/194; 604/103.06
(58) Field of Search ........................ 604/96.01, 101.01, 604/101.02, 103.05, 103, 103.06, 915, 919, 921, 108; 606/192, 194; 623/1.11

(56) References Cited

U.S. PATENT DOCUMENTS

| | | | |
|---|---|---|---|
| 5,358,486 A | * 10/1994 | Saab | 604/103.13 |
| 5,374,473 A | 12/1994 | Knox et al. | |
| 5,409,495 A | * 4/1995 | Osborn | 623/1.11 |
| 5,752,934 A | 5/1998 | Campbell et al. | |
| 5,788,626 A | 8/1998 | Thompson | |
| 5,868,704 A | 2/1999 | Campbell et al. | |
| 6,016,848 A | 1/2000 | Egres, Jr. | |
| 6,120,477 A | 9/2000 | Campbell et al. | |
| 6,428,506 B1 | 8/2002 | Simhambhatla et al. | |
| 6,602,224 B1 | 8/2003 | Simhambhatla | |

FOREIGN PATENT DOCUMENTS

| | | |
|---|---|---|
| WO | WO 95/05555 | 2/1995 |
| WO | WO 97/02791 | 1/1997 |

* cited by examiner

*Primary Examiner*—LoAn H. Thanh
(74) *Attorney, Agent, or Firm*—Fulwider Patton Lee & Utecht LLP (57) ABSTRACT

A catheter balloon or other expandable tubular medical device or component, having at least a first layer with a first section and a second section longitudinally compacted by more than the first section. In a presently preferred embodiment, the second section of the first layer extends at least in part along a central portion of the length of the first layer. The longitudinal compaction of the material of the first layer preferably results in a balloon or other expandable tubular medical device or component having improved performance characteristics such as compliance and dimensional stability. One aspect of the invention is directed to a method of longitudinally compacting a porous polymeric tube incrementally along the length of the tube, to compact sections of the tube.

23 Claims, 4 Drawing Sheets

COMPACTED CATHETER BALLOON AND METHOD OF INCREMENTAL COMPACTION

BACKGROUND OF THE INVENTION

This invention generally relates to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. A tubular cover formed of synthetic or natural material may be present on an outer or inner surface of the stent. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

In the design of catheter balloons, characteristics such as strength, compliance, and profile of the balloon vary depending on the desired use of the balloon catheter. A variety of polymeric materials are conventionally used in catheter balloons, and the balloon material and manufacturing procedure are chosen to provide the desired balloon characteristics. Use of polymeric materials such as PET that do not stretch appreciably consequently necessitates that the balloon is formed by blow molding, and the deflated balloon material is folded around the catheter shaft in the form of wings, prior to inflation in the patient's body lumen. However, it can be desirable to employ balloons, referred to as formed-in-place balloons, that are not folded prior to inflation, but which are instead expanded to the working diameter within the patient's body lumen from a generally cylindrical or tubular shape (i.e., essentially no wings) that conforms to the catheter shaft.

Catheter balloons formed of expanded polytetrafluoroethylene (ePTFE) expanded in place within the patient's body lumen without blow molding the ePTFE tubing have been disclosed. Prior disclosed methods of forming an ePTFE balloon involved wrapping a sheet of ePTFE on a mandrel and heating the wrapped sheet to fuse the layers of wrapped material together to form a tube. The resulting ePTFE tube may be subsequently heated in one or more additional heating steps and otherwise further processed, and typically combined with a nonporous liner to complete formation of the balloon. It would be a significant advance to provide an ePTFE tube for forming a balloon or other expandable medical device or component, with improved performance characteristics and manufacturability.

SUMMARY OF THE INVENTION

This invention is directed to a catheter balloon or other expandable tubular medical device or component, having at least a first layer with a first section, and a second section longitudinally compacted by more than the first section. The second section of the first layer is typically longitudinally adjacent to the first section of the first layer, and preferably extends at least in part along a central portion of the length of the first layer. The longitudinal compaction of the material of the first layer in accordance with the invention results in a balloon or other device or component having improved performance characteristics such as compliance and dimensional stability. One aspect of the invention is directed to a method of longitudinally compacting a porous polymeric tube incrementally along the length of the tube, to compact sections of the tube.

Longitudinal compaction of a section of the first layer decreases the length of the section and preferably also decreases the porosity of the material forming the section, so that in one embodiment, the first layer first section, which is more highly longitudinally compacted than the first layer second section, has a lower porosity than the first layer second section. The degree of longitudinal compaction is expressed herein as a percentage length reduction. Thus, a section having a precompaction length (i.e., the length of the section just prior to being longitudinally compacted in accordance with the invention) of 2 cm, which is subsequently longitudinally compacted to a length of 1 cm, has a longitudinal compaction of 50% (i.e., (2 cm−1 cm)÷2 cm).

In a presently preferred embodiment, the medical device tubular component is an inflatable balloon for a catheter. A balloon which embodies features of the invention can be used on a variety of suitable balloon catheters including coronary and peripheral dilatation catheters, stent delivery catheters, drug delivery catheters and the like. A balloon catheter of the invention generally comprises an elongated shaft having a proximal shaft section, a distal shaft section, at least a first lumen, and a balloon on a distal shaft section with an interior in fluid communication with the first lumen of the shaft. Although discussed below primarily in terms of the embodiment in which the medical device component is an inflatable member such as a balloon for a catheter, it should be understood that other expandable medical devices and components are included within the scope of the invention, including stent covers and vascular grafts.

The catheter balloon typically has a proximal and a distal skirt section secured to the shaft, an inflatable working length section, an inflatable proximal section between the proximal skirt section and the working length which inflates to a tapered configuration ("the proximal tapered section"), and an inflatable distal section between the distal skirt section and the working length which inflates to a tapered configuration ("the distal tapered section"). It should be understood that in at least in one embodiment the balloon is not blow molded or otherwise preexpanded into the inflated configuration prior to use. Thus, the "proximal and distal tapered sections" typically do not have a tapered configuration prior to the balloon being inflated during use of the balloon catheter.

In a presently preferred embodiment, the section of the first layer located at the central working length section of the balloon (hereafter the first layer working section) has a longitudinal compaction greater than the sections of the first layer located at the proximal and distal tapered sections of the balloon (hereafter the first layer tapered sections). The inflated tapered sections of the balloon form the transition between the skirt sections bonded to the shaft and the inflated working length of the balloon. Thus, depending on the length and the diameter of the inflated tapered sections, this transition can range from a gradual shallow taper to a short sharp transition. In one embodiment, the first layer tapered sections have a longitudinal compaction such that, when inflated, the tapered sections have a desired length and a desired inflated outer diameter tapering between the inflated working length to the skirt section, to decrease the hoop stress and stress concentration at the end of the skirt section. Thus, the rupture pressure of the balloon is increased by increasing the rupture pressure of the bond between the skirt section and the shaft. Specifically, in one embodiment, in the inflated configuration, the tapered sections taper at an angle of about 5° to about 45°, and with an inflated length of about 1 to about 5 mm. Thus, in one embodiment, the longitudinal compaction percentages of the sections are selected to provide a balloon having a desired inflated dimension and shape.

Additionally, in one embodiment, axial shrinkage of the balloon sections which would otherwise occur during inflation of the balloon is decreased by the longitudinal compaction of the first layer sections. Specifically, for no axial shrinkage or a minimal amount of axial shrinkage (i.e., less than 5%), the presently preferred the inflatable length of a porous polymeric layer of a balloon has a longitudinal compaction of about 10% to about 60%, preferably about 20% to about 50%. When not compacted, the axial shrinkage is believed to be about 10% to about 30% of the length of the balloon.

In one embodiment, the sections of the first layer located at the skirt sections of the balloon (hereafter the first layer skirt sections) have a longitudinal compaction which is less than or at least not greater than the longitudinal compaction of the first layer tapered sections. In one embodiment the first layer skirt sections are not longitudinally compacted, and thus have a longitudinal compaction of 0%. The first layer skirt section preferably has improved flexibility and low profile due to the low or zero percent longitudinal compaction of the skirt section. The skirt sections of the first layer extend along the section of the balloon secured to the shaft. However, the skirt sections of the first layer are not necessarily directly secured to the shaft, and may instead have at least a portion secured to a section of a second (inner) layer of the balloon which is directly secured to the shaft. The terminology "directly secured" to the shaft should be understood to include a variety of bonding methods including fusion and adhesive bonding.

In a presently preferred embodiment, the polymeric material of the first layer of the balloon comprises a polymer having a porous structure, which in one embodiment is selected from the group consisting of expanded polytetrafluoroethylene (ePTFE), ultra high molecular weight polyolefin such as ultra high molecular weight polyethylene, and porous polyolefins such as polyethylene and polypropylene, and porous polyurethane. In one embodiment, the porous material has a node and fibril microstructure. For example, ePTFE and ultra high molecular weight polyethylene typically have a node and fibril microstructure, and are not melt extrudable. The node and fibril microstructure, when present, is produced in the material using conventional methods. However, a variety of suitable polymeric materials can be used in the method of the invention including conventional catheter balloon materials which are melt extrudable. In one presently preferred embodiment, the polymeric material is typically not formed into a balloon by conventional balloon blow molding, and is instead formed into a balloon by heat fusing wrapped layers of the polymeric material together to form a tubular member. Porous materials such as ePTFE and ultrahigh molecular weight polyethylene typically require a nonporous second layer or liner when used to form an inflatable balloon. Thus, the balloon or other tubular medical device or component having a first layer with longitudinally compacted sections, should be understood to include an embodiment where the first layer forms at least a layer of a multilayered catheter balloon. The balloon first layer is typically longitudinally compacted before being secured to the balloon second layer, and the second layer is typically not longitudinally compacted.

A method of making a first layer of an expandable tubular medical device or component having at least one layer, generally comprises individually compacting incremental segments of a porous polymeric tube to incrementally compact the porous polymeric tube. In one embodiment, the method comprises placing a porous polymeric tube having a length and an outer diameter on a mandrel, with a diameter limiting member around at least a portion of the tube. In one embodiment, the diameter limiting device is selected from the group consisting of a die, a polymeric tube, and a sheet of polymeric material wrapped around the porous polymeric tube. A mold may also be used as the diameter limiting device, although preferably such that the mold uniformly limits the diameter of the segment of the tube during compaction, to thereby produce uniform compaction along the length of the individual segment avoiding buckling of the segment into an accordion-like configuration during compaction. At least a first compactor member is releasably secured to the tube at a first location on the tube, the secured compactor member being slidably disposed relative to the mandrel, and the compactor member is moved a distance, to thereby compact a first segment of the tube which is within the diameter limiting member and which has a length less than the entire length of the tube. The compactor member is released and repositioned on the tube at a second location on the tube, and the compactor member is releasably secured to the tube at the second location. The compactor member is then moved a distance, to compact a second segment of the tube which is adjacent to the first segment and which is within the diameter limiting member and which has a length less than the entire length of the tube. In one embodiment, the incremental compaction method of the invention produces uniform compaction along the length of the porous polymeric tube. In an alternative embodiment, one or more segments are compacted by an amount different than the first segment, so that the incremental compaction method of the invention produces variable compaction along the length of the porous polymeric tube.

The invention provides a catheter balloon or other expandable tubular medical device or component, having improved performance characteristics due to the longitudinal compaction of sections of the porous polymeric layer. In one embodiment, the compacted sections provide a balloon having an inflated configuration with a desired shape and dimensions, and with reduced stress at the skirt sections. An improved method of compacting porous polymeric material during formation of a tubular medical device or component, provides controllable incremental compaction of the porous polymeric material to produce uniform or variable compaction along the length of the tube. These and other advantages of the invention will become more apparent from the following detailed description of the invention and the accompanying exemplary drawings.

DETAILED DESCRIPTION OF THE INVENTION

Figures 1, 2, 3:
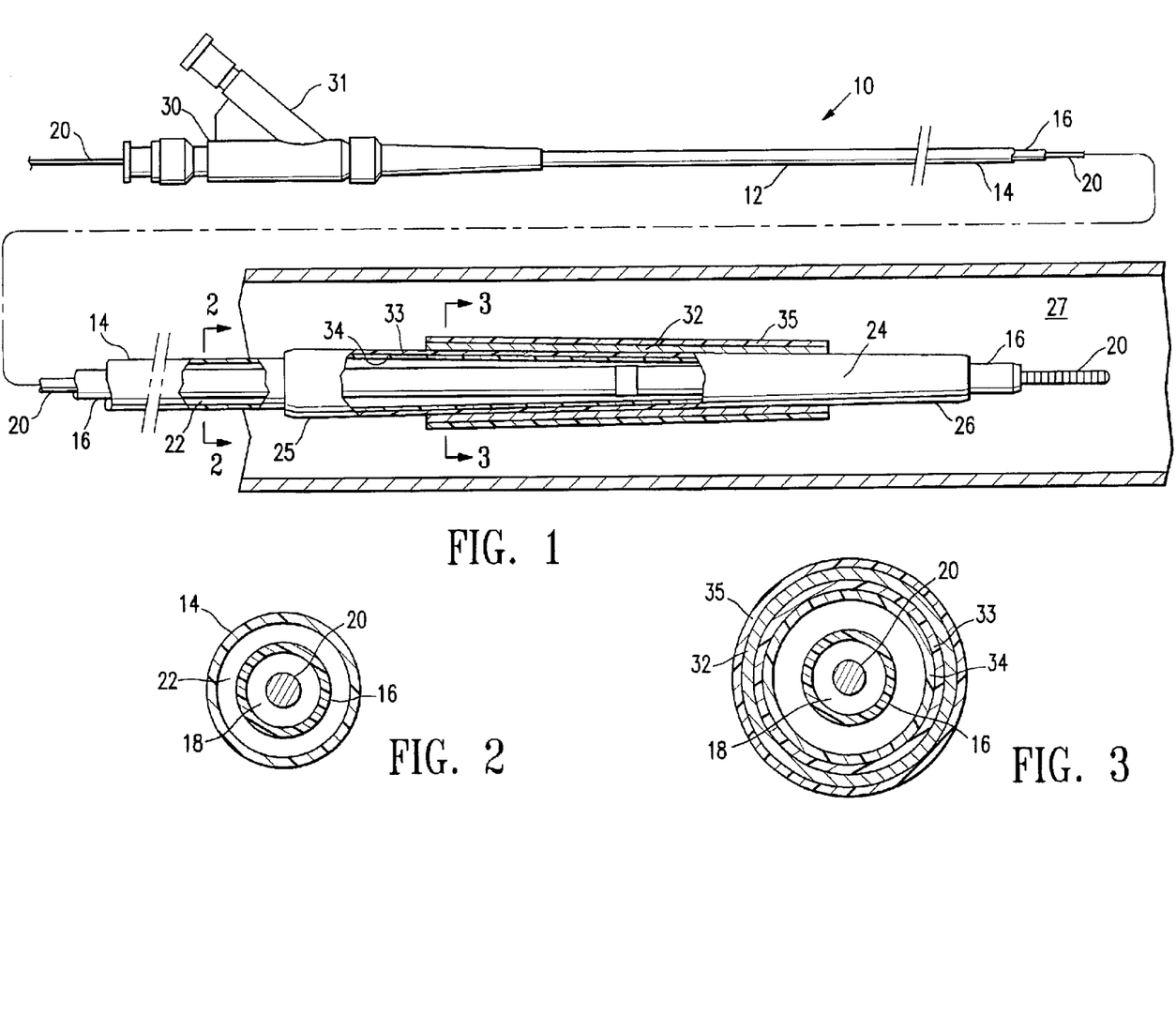
FIG. 1 is an elevational view, partially in section, of a stent delivery balloon catheter embodying features of the invention.
FIG. 2 is a transverse cross sectional view of the balloon catheter shown in FIG. 1, taken along line 2—2.
FIG. 3 is a transverse cross sectional view of the balloon catheter shown in FIG. 1, taken along line 3—3.

FIG. 1 illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section view of the distal end of the catheter shown in FIG. 1, taken along line 2—2. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that its interior is in fluid communication with inflation lumen 22. An adapter 30 at the proximal end of catheter shaft 12 is configured to provide access to guidewire lumen 18, and to direct inflation fluid through arm 31 into inflation lumen 22. FIG. 1 illustrates the balloon 24 in a low profile tubular configuration prior to complete inflation, with an expandable stent 32 having a stent cover 35, mounted on the balloon 24 for delivery within a patient's body lumen 27. The distal end of catheter 10 may be advanced to a desired region of the patient's body lumen 27 in a conventional manner, and balloon 24 inflated to expand covered stent 32, and the balloon deflated, leaving covered stent 32 implanted in the body lumen 27. FIG. 3 illustrates a transverse cross section view of the distal end of the catheter shown in FIG. 1, taken along line 3—3.

In the embodiment illustrated in FIG. 1, balloon 24 has a first layer 33 and a second layer 34. In a presently preferred embodiment, the balloon 24 first layer 33 comprises a microporous polymeric material, and preferably a microporous polymeric material having a node and fibril microstructure, such as ePTFE. In the embodiment illustrated in FIG. 1, first layer 33 is formed of ePTFE, and the second layer 34 is formed of a polymeric material preferably different from the polymeric material of the first layer 33. Although discussed below in terms of one embodiment in which the first layer 33 is formed of ePTFE, it should be understood that the first layer may comprise other materials, including ultrahigh molecular weight polyethylene. The second layer 34 is preferably formed of an elastomeric material, such as polyurethane elastomers, silicone rubbers, styrene-butadiene-styrene block copolymers, polyamide block copolymers, and the like. In a preferred embodiment, layer 34 is an inner layer relative to layer 33, although in other embodiments it may be an outer layer. Layer 34 formed of an elastomeric material limits or prevents leakage of inflation fluid through the microporous ePTFE to allow for inflation of the balloon 24, and expands elastically to facilitate deflation of the balloon 24 to a low profile deflated configuration. The elastomeric material forming layer 34 may consist of a separate layer which neither fills the pores nor disturbs the node and fibril structure of the ePTFE layer 33, or it may at least partially fill the pores of the ePTFE layer.

Figure 4:
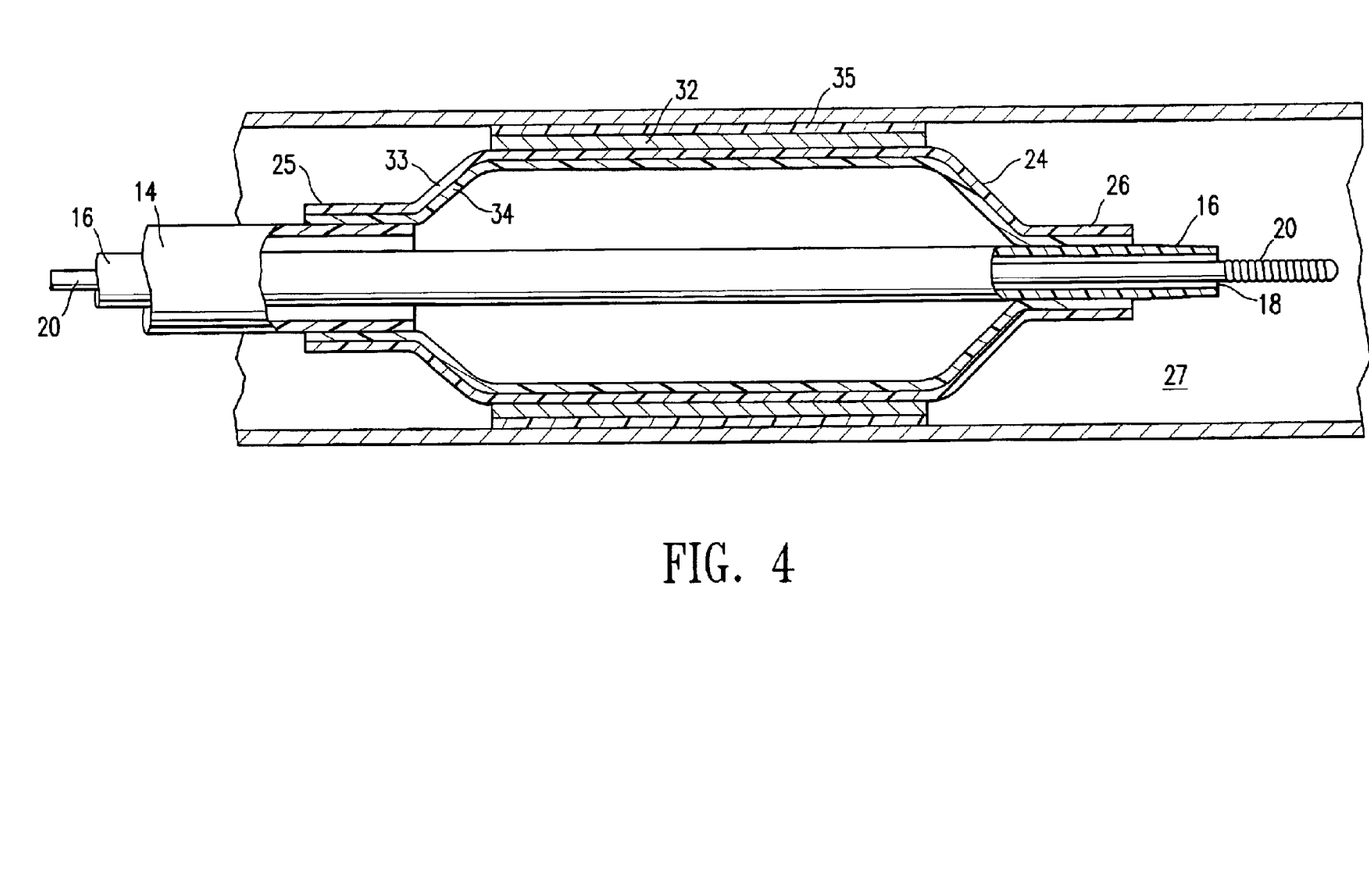
FIG. 4 illustrates the balloon catheter of FIG. 1, with the balloon inflated.

FIG. 4 illustrates the balloon catheter 10 of FIG. 1, with the balloon in an inflated configuration. The inflated balloon 24 has a central working section with covered stent 32 thereon, a proximal tapered section between the working section and the proximal skirt section 25, and a distal tapered section between the distal skirt section 26 and the working section. The section of the first layer 33 extending along the working section of the balloon is hereafter referred to as the first layer working section. Similarly, the first layer proximal and distal tapered sections refer to the sections of the first layer 33 extending along the proximal and distal tapered sections of the balloon, and the first layer skirt sections refer to the sections of the first layer 33 extending along the balloon skirt sections 25, 26. In one presently preferred embodiment, the inflated first layer working section has a length of about 8 to about 80 mm, the inflated first layer proximal tapered section has a length of about 1 to about 5 mm, and the inflated first layer distal tapered section has a length of about 1 to about 5 mm. Although the balloon 24 is illustrated in FIG. 4 with a conventional inflated configuration having a cental working length between two tapered inflatable sections, it should be understood that the inflated balloon may have a variety of suitable configurations including balloon configurations specially shaped for a particular anatomy such as a focal balloon configuration, a conical balloon configuration, and the like, as are conventionally known to one of skill in the art.

The first and second layers 33, 34 of balloon 24 each extend from the proximal skirt section 25 of the balloon to the distal skirt section 26 of the balloon. The first layer 33 can have a length which is the same as or a shorter than the length of the second layer 34, or alternatively, can have end sections which extend beyond the end sections of the second layer 34 and directly onto the shaft. FIG. 4 illustrates one embodiment in which the layers 33, 34 of the balloon have the same length, so that the skirt sections 25, 26 consist of end sections of the second (inner) layer 34 having an inner surface bonded to the shaft, and end sections of the first (outer) layer 33 having an inner surface bonded to the end sections of the second layer 34. However, in an alternative embodiment (not shown), the ends of the first layer 33 extend beyond the end sections of the second layer 34 and onto the shaft 12, so that the skirt sections 25, 26 are also formed in part by end sections of the first layer 33 which extend beyond the end sections of the second layer 34 and bond directly to the shaft 12 without the second layer 34 therebetween. The lengths of the first layer skirt sections will vary depending on a variety of factors including the method of bonding the balloon to the shaft. In one presently preferred embodiment, the first layer proximal skirt section has a length of about 1 to about 5 mm, and the first layer distal skirt section has a length of about 1 to about 5 mm.

The ePTFE layer 33 of balloon 24 has sections with different amounts of longitudinal compaction, at least prior to being inflated. Preferably, the ePTFE layer 33 has a first section, and a second section longitudinally adjacent to the first section and extending at least in part along a central portion of the length of the balloon, the second section being longitudinally compacted by more than the first section. In a presently preferred embodiment, the second section of the ePTFE layer 33 is located at the first layer working length (i.e., the section of the first layer 33 extending along the working section of the inflated balloon), and the first section of the ePTFE layer 33 is located at the first layer proximal or distal tapered sections. In a presently preferred embodiment, the section of the first layer located at the working length of the balloon has a greater longitudinal compaction than the sections of the first layer located at both the proximal and the distal inflated tapered sections of the balloon. Thus, in one embodiment, the central working section of the ePTFE layer 33 has a greater longitudinal compaction than the remaining inflatable sections of the ePTFE layer 33.

In one embodiment, the first layer working section has a longitudinal compaction of about 10% to about 60%, more specifically about 20% to about 50% of a prelongitudinal compaction length of the section, and the first layer tapered sections have a longitudinal compaction of about 10% to about 40%, more specifically about 15% to about 30% of a prelongitudinal compaction length of the sections. The percent longitudinal compaction values should be understood to refer to values existing prior to inflation of the balloon, and defined as a percentage length reduction from before to after the compaction process. For example, longitudinally compacting an ePTFE tube so that a section corresponding to the first layer working section is compacted from a prelongitudinal compaction length of about 2.86 cm to a compacted length of about 2 cm, produces a 2 cm first layer working section having a longitudinal compaction of about 30% prior to inflation of the balloon.

The first layer skirt sections have a longitudinal compaction which is not greater than, and preferably is less than the longitudinal compaction of the first layer tapered sections. In a presently preferred embodiment, the first layer skirt sections are not longitudinally compacted, and thus have a longitudinal compaction of 0%. In one embodiment, the first layer skirt sections have a longitudinal compaction of about 0% to about 30%, more specifically about 10% to about 20%.

Thus, in one presently preferred embodiment, a balloon ePTFE layer having a post-compaction working length of 20 mm compacted by 40%, post-compaction tapered sections of 2 mm compacted by 30%, and post-compaction skirt sections of 2 mm compacted by 20%, had an original pre-compaction working length of 33.3 mm, original pre-compaction tapered sections of 2.86 mm, and original pre-compaction skirt sections of 2.5 mm.

The first layer working section, prior to inflation of the balloon 24, preferably has a lower porosity than the first layer proximal and distal tapered sections and lower than the first layer proximal and distal skirt sections. Specifically, in one embodiment, the first layer working section (prior to inflation) has a porosity about 0 to about 40% lower than a porosity of the first layer proximal and distal tapered sections, and about 10 to about 60% lower than a porosity of the first layer proximal and distal skirt sections. In one embodiment, the first layer proximal and distal tapered sections have a porosity lower than the first layer proximal and distal skirt sections, and specifically about 10 to about 30% lower than the porosity of the first layer proximal and distal skirt sections.

The ePTFE layer 33 is preferably formed according to a method in which an ePTFE tube used to form layer 33 is incrementally compacted. Specifically, the individual sections of layer 33 having specific longitudinal compaction values (e.g., the working length, and the proximal and distal tapered sections) are each produced by compacting multiple smaller length portions of the tube. For example, to produce a working length having a length of 2 cm and a longitudinal compaction of about 30%, 3 portions each having an initial precompaction length of 0.95 cm would each be successively compacted to a compacted length of 0.65 cm (i.e., (0.7)(0.95 cm)), to collectively produce the 2 cm working length having a 30% longitudinal compaction.

FIGS. 5a–d illustrate an assembly with a polymeric tube 40 during incremental longitudinal compaction of the tube 40 in a method which embodies features of the invention. The polymeric material of the tube 40 is ePTFE in the embodiment in which the tube forms ePTFE layer 33 of the balloon 24 of FIG. 1. The tube 40 may be provided with uniform longitudinal compaction such that each incremental segment is compacted by the same amount, or alternatively, it may be provided with variable compaction in which one or more incremental segments are longitudinally compacted by different amounts.

In the embodiment illustrated in FIG. 5, the tube 40 is on a mandrel 41 with a portion of the tube 40 in a die 42 having an inlet 43 and an outlet 44. The mandrel 41 may optionally have a polymeric jacket (not shown) on an outer surface of the metallic body. A compactor member 45 is releasably secured to the tube at a location on the tube 40 spaced from the die inlet 43 by a distance "d". In the embodiment of FIG. 5, the compactor member 45 comprises a block with a bore configured to surround and clamp onto the tube 40 with the mandrel 41 therein, such as with a collet-type clamping mechanism. However, a variety of suitable compactor members may be used including a hydraulic clamp. The compactor member 45 is secured to the tube 40 such that it is slidably disposed relative to the mandrel within the tube. A fixing member 46 releasably secures the tube 40 to the mandrel at a location on the tube adjacent the outlet 44 of the die 42. In the embodiment of FIG. 5, the fixing member 46 comprises a block similar to the compactor member 45, with a bore configured to surround and clamp onto the tube 40 and mandrel 41 therein. With the compactor member 45 releasably secured to the tube 40 the distance "d" from the inlet 43 of the die 42, a first segment "$S_1$" of the tube 40 is located between the compactor member 45 and the outlet 44 of the die 42, as illustrated in FIG. 5a. The compactor member 45 is then moved toward the inlet 43 of the die 42 to compact the first segment "$S_1$" of the tube 40 into the die, thereby forming compacted segment "$CS_1$", as illustrated in FIG. 5b. The compacted segment is illustrated in the figures by closer-spaced cross hatching. The difference between the original precompacted length "$S_1$" of the segment, and the compacted length "$CS_1$" of the segment, expressed as a percentage of the original precompacted length "$S_1$", is the percent longitudinal compaction of the segment. The die may be heated to thereby heat the compacted segment "$CS_1$" in the die, to heat stabilize the compacted segment in the compacted configuration. In a presently preferred embodiment, the die is heated to an elevated temperature of about 320° C. to about 400° C., preferably about 350° C. to about 370° C. to heat stabilize the compacted segment. The compactor member 45 and fixing member 46 are then released, and the tube 40 is repositioned by sliding the compacted segment "$CS_1$" through the die outlet 44 to place another noncompacted portion of the tube 40 in the die lumen, as illustrated in FIG. 5c. With the compactor member 45 and fixing member 46 again releasably secured to the tube 40, the second segment "$S_2$" is compacted as outlined above. The second segment "$S_2$" may be compacted by the same amount as the first segment "$S_1$" in order to continue formation of a first compacted section, or it may be compacted by a different amount in order to provide for a second compacted section. FIG. 5d illustrates the assembly after the compaction of the second segment "$S_2$" to produce compacted segment "$CS_2$", with the compactor member and fixing member again repositioned and secured on the tube 40, ready for compaction of a third segment "$S_3$".

During compaction, the compactor member 45 may be moved the entire distance "d" to the die inlet 43, or alternatively, it may be moved a distance less than "d" depending on the amount of longitudinal compaction desired for the segment being compacted. For example, in the embodiments illustrated in FIGS. 5a–d, the length of the first, second, and third segments $S_1$, $S_2$, $S_3$ are approximately equal, so that the compactor member 45 could be moved the entire distance "d" to produce an amount of compaction in one of the segments, and moved a distance less than "d" in order to produce a smaller amount of compaction in one or more of the remaining segments.

The inner diameter of the inner chamber of die 42 is sized so that the tube 40 compacts without the outer diameter of the tube increasing. The inner diameter of the inner chamber of die 42 is typically about equal to the outer diameter of the tube 40 on the mandrel 41. Alternatively, the inner diameter of the inner chamber of die 42 may be smaller than the outer diameter of the tube 40 on the mandrel 41, so that it provides resistance to movement of the tube 40 therein to increase the percent compaction of the tube 40. The length of the inner chamber of the die 42 in which tube is compacted is typically about 1 to about 5 cm, preferably about 2 to about 3 cm. The length of the tube 40 is typically about 4 to about 20 cm to produce a layer 33 of a balloon having a length of about 2 to about 10 cm. The length of the segments $S_1$, $S_2$, $S_3$ is typically about 5 to about 25 mm, preferably about 5 to about 15 mm. The length of the segment is preferably sufficiently short such that the segment compacts uniformly along the length of the segment and without buckling.

After being longitudinally compacted, the tube 40 may be heat treated or otherwise further processed and secured to the second layer 34, to complete formation of the balloon 24. The tube 40 is typically longitudinally stretched prior to being longitudinally compacted, as for example by being placed on a mandrel and pulled at either end to stretch down on to the mandrel, although it can be longitudinally stretched using a variety of suitable methods. With the tube 40 restrained in the longitudinally stretched configuration, the tube 40 is typically heated, to stabilize the tube in the stretched configuration prior to being longitudinally compacted.

Figure 5A:
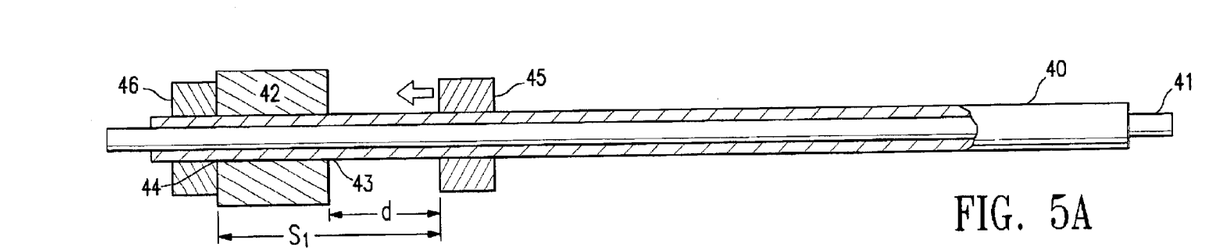
FIGS. 5a–d illustrate an assembly of a tube of polymeric material on a mandrel, partially in section, during longitudinal compaction of portions of the tube to form a layer of the balloon of FIG. 1, in a method which embodies features of the invention, in which a block is moved to compact a portion of the tube into a die.
Figure 5B:
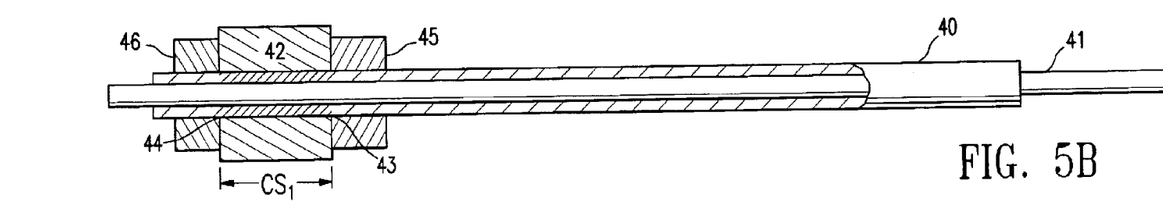
Figure 5C:
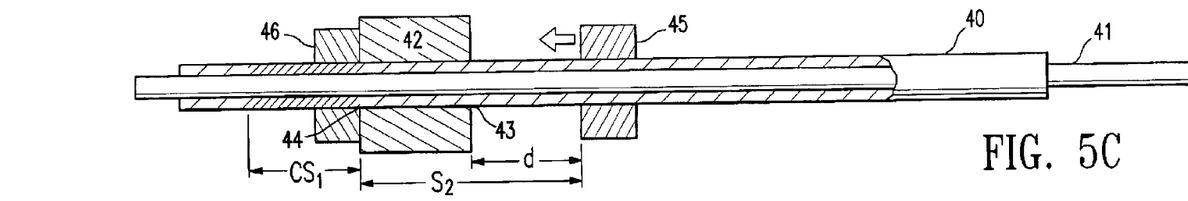
Figure 5D:
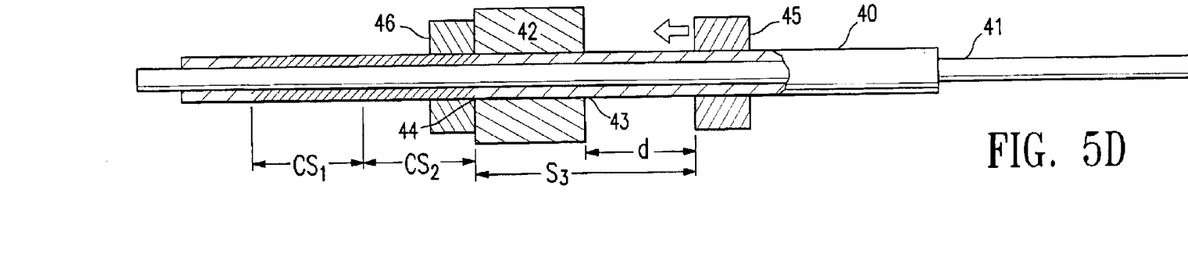
Figure 6A:
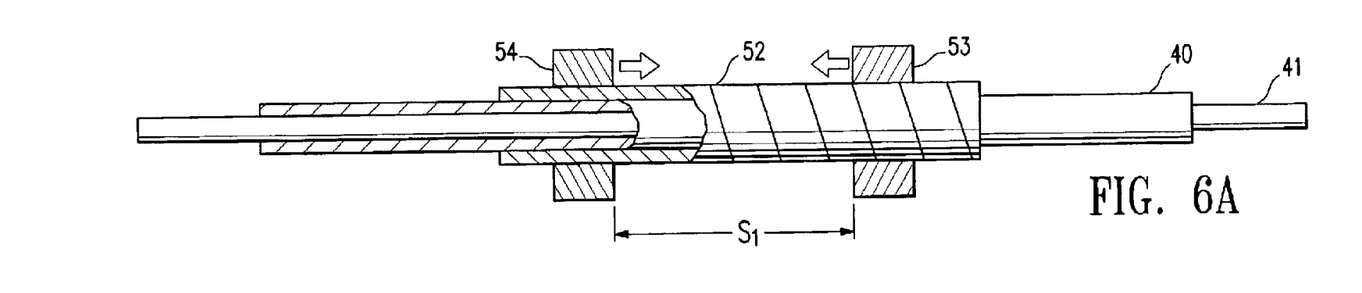
FIGS. 6a–c illustrate an assembly of a tube of polymeric material on a mandrel, partially in section, during longitudinal compaction of portions of the tube to form a layer of the balloon of FIG. 1, in an alternative method which embodies features of the invention, in which two blocks are moved together to compact a portion of the tube in a diameter limiting member between the blocks.
Figure 6B:
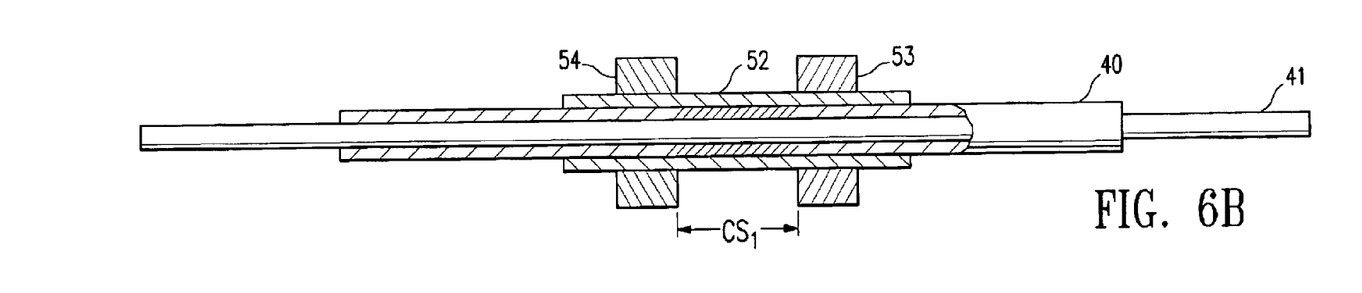
Figure 6C:
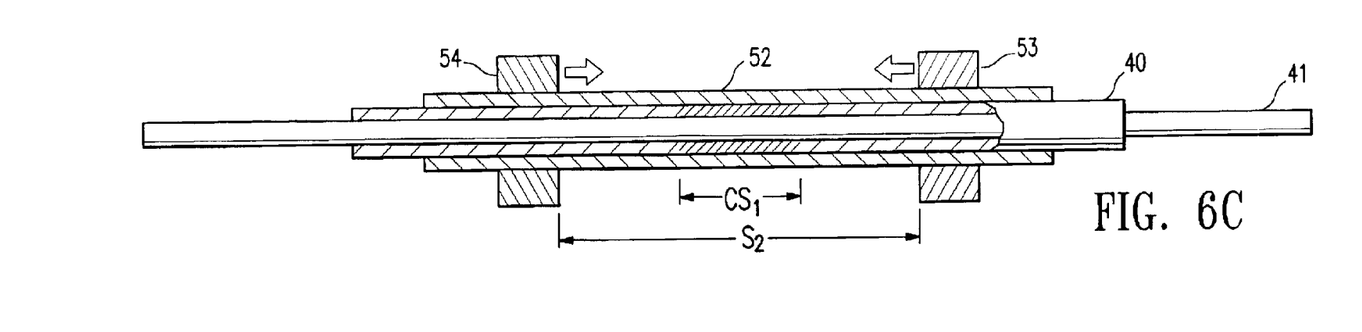

FIGS. 6a–c illustrate an assembly of polymeric tube 40 on mandrel 41 during incremental longitudinal compaction of the tube in an alternative method which embodies features of the invention. Similar to the embodiment of FIG. 5, the tube 40 may be provided with uniform longitudinal compaction, or alternatively, with variable compaction.

In the embodiment illustrated in FIG. 6, the tube 40 is on a mandrel 41 with a portion of the tube 40 in a diameter limiting member 52 comprising a sheet of polymeric material wrapped around the tube 40. In a presently preferred embodiment, the sheet of polymeric material forming the diameter limiting member 52 is ePTFE, although other polymeric materials may be used, including Teflon, and polyolefins such as high density polyethylene (HDPE), low density polyethylene (LDPE), and linear low density polyethylene (LLDPE). At least a first compactor member 53 is releasably secured at a first location to the tube and slidably disposed relative to the mandrel 41. In the embodiment of FIG. 6, the first compactor member 53 is a block similar to the block of the embodiment of FIG. 5. In the embodiment of FIG. 6, a second compactor member 54 is releasably secured at a second location to the tube 40 longitudinally spaced apart from the first compactor member 53 with at least a portion of the diameter limiting device 52 therebetween. With the first and second compactor members 53, 54 releasably secured to the tube 40 a distance apart, a first segment "$S_1$" of the tube 40 is located between the compactor members, as illustrated in FIG. 5a. The first and second compactor members 53, 54 are then moved toward one another toward a center of the length of the tube 40 to longitudinally compact the first segment "$S_1$" therebetween in the diameter limiting device 52, thereby forming compacted segment "$CS_1$", as illustrated in FIG. 6b. The compactor members 53, 54 are then released and resecured to the tube. In a presently preferred embodiment, the compactor members 53, 54 are resecured to the tube 40 at locations further apart on the tube and closer to the ends of the tube 40, with second segment "$S_2$" greater than "$S_1$" therebetween, as illustrated in FIG. 6c. The compactor members 53, 54 are illustrated in FIG. 6c ready to be moved toward one another toward a center of the length of the tube 40, to longitudinally compact the second segment "$S_2$" therebetween in the diameter limiting device 52. The ePTFE tape 52 typically has a length sufficient to cover the entire length of the tube 40 to be compacted, so that the ePTFE tape 52 does not have to be removed and replaced with a longer length of ePTFE tape 52 between the compaction of each individual segment of tube 40. In alternative embodiments (not shown) using alternative diameter limiting members such as a tube, die, or mold, the diameter limiting device is typically released from the compacted segment and a longer diameter limiting device is secured to the tube to accommodate the longer length of the next segment to be compacted. The compacted tube 40 may be heated to heat stabilize the compacted segments, as discussed above in relation to the embodiment of FIG. 5, as for example by traversing a heating nozzle along the length of the compacted segments. In the illustrated embodiment in which the diameter limiting member 52 is ePTFE tape wound around the tube 40, the tube may be heated at the end of the compaction of the final segment rather than after each individual compaction, because the ePTFE tape 52 is typically not removed between the compaction of each individual segment of the tube 40. The length of the segments being compacted is typically about 10 to about 50 mm, preferably about 20 to about 30 mm.

In an alternative embodiment (not shown), a fixing member is used in place of the second compaction member 54, which is releasably secures the tube 40 to the mandrel 41, so that compacting the segment therebetween comprises moving the first compactor member 53 toward the fixing member. The distance between the first compaction member 53 and the fixing member is then increased, for compacting another segment of the tube as described above.

To the extent not previously discussed herein, the various catheter components may be formed and joined by conventional materials and methods. For example, the outer and inner tubular members 14, 16 can be formed by conventional techniques, such as by extruding and necking materials found useful in intravascular catheters such a polyethylene, polyvinyl chloride, polyesters, polyamides, polyimides, polyurethanes, and composite materials.

The length of the balloon catheter 10 is generally about 108 to about 200 centimeters, preferably about 137 to about 145 centimeters, and typically about 140 centimeters for PTCA. The outer tubular member 14 has an outer diameter (OD) of about 0.017 to about 0.036 inch (0.43–0.91 mm), and an inner diameter (ID) of about 0.012 to about 0.035 inch (0.30–0.89 mm). The inner tubular member 14 has an OD of about 0.017 to about 0.026 inch (0.43–0.66 mm), and an ID of about 0.015 to about 0.018 inch (0.38–0.46 mm) depending on the diameter of the guidewire to be used with the catheter. The balloon 24 has a length of about 8 mm to about 80 mm, typically about 8 mm to about 38 mm, and an inflated working diameter of about 1.5 mm to about 20 mm, typically about 2 mm to about 10 mm.

While the present invention has been described herein in terms of certain preferred embodiments, those skilled in the art will recognize that modifications and improvements may be made without departing from the scope of the invention. For example, although the embodiment illustrated in FIG. 1 is an over-the-wire stent delivery catheter, balloons of this invention may also be used with other types of intravascular catheters, such as rapid exchange balloon catheters. Rapid exchange catheters generally comprise a distal guidewire port in a distal end of the catheter, a proximal guidewire port in a distal shaft section distal of the proximal end of the shaft and typically spaced a substantial distance from the proximal end of the catheter, and a short guidewire lumen extending between the proximal and distal guidewire ports in the distal section of the catheter. While individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising:
   a) an elongated shaft having a proximal end, a distal end, and at least a first lumen; and
   b) a balloon on a distal shaft section, having an interior in fluid communication with the first lumen, a proximal end, a distal end, a length extending from the proximal to the distal end of the balloon, and having at least a first layer with a first section, and with a second section longitudinally adjacent to the first section and extending at least in part along a central portion of the length of the balloon, the first layer second section being longitudinally compacted by more than the first layer first section, so that in a noninflated configuration prior to inflation of the balloon the second section has a lower porosity than the first section.

2. The balloon catheter of claim 1 wherein the balloon has a proximal skirt section secured to the shaft, a distal skirt section secured to the shaft, an inflatable working section, an inflatable proximal section which inflates to a tapered configuration and which is between the proximal skirt section and the inflatable working section, and an inflatable distal section which inflates to a tapered configuration and which is between the distal skirt section and the inflatable working section, and the second section of the first layer is located at the inflatable working section of the balloon.

3. The balloon catheter of claim 2 wherein the first section of the first layer is located at the inflatable proximal section of the balloon.

4. The balloon catheter of claim 3 wherein the second section of the first layer is longitudinally compacted by more than a section of the first layer located at the inflatable distal section of the balloon.

5. The balloon catheter of claim 4 wherein the sections of the first layer located at the inflatable proximal and distal sections of the balloon are longitudinally compacted by more than sections of the first layer located at the proximal and distal skirt sections of the balloon.

6. The balloon catheter of claim 3 wherein the second section of the first layer has a longitudinal compaction of about 10% to about 60% of the section's pre-longitudinal compaction length.

7. The balloon catheter of claim 3 wherein the section of the first layer located at the inflatable proximal section has a longitudinal compaction of about 10% to about 40% of the section's pre-longitudinal compaction length.

8. The balloon catheter of claim 3 wherein the section of the first layer located at the inflatable distal section has a longitudinal compaction of about 10% to about 40% of the section's pre-longitudinal compaction length.

9. The balloon catheter of claim 3 wherein the sections of the first layer located at the proximal and distal skirt sections each have a longitudinal compaction of about 0% to about 30% of the section's pre-longitudinal compaction length.

10. The balloon catheter of claim 1 wherein the sections of the first layer located at the proximal and distal skirt sections are not longitudinally compacted.

11. The balloon catheter of claim 3 wherein the inflatable proximal section extending between the proximal skirt section and the working length has an inflated length of about 1 to about 5 mm.

12. The balloon catheter of claim 3 wherein the inflatable distal section extending between the distal skirt section and the working length has an inflated length of about 1 to about 5 mm.

13. The balloon catheter of claim 3 wherein the distal skirt section has a length of about 1 to about 5 mm, and the proximal skirt section has a length of about 1 to about 5 mm.

14. The balloon catheter of claim 2 wherein the second section of the first layer has a porosity about 0 to about 40% lower than a porosity of the sections of the first layer located at the inflatable proximal and distal sections of the balloon.

15. The balloon catheter of claim 2 wherein the second section of the first layer has a lower porosity than the sections of the first layer located at the proximal and distal skirt sections of the balloon.

16. The balloon catheter of claim 2 wherein the sections of the first layer located at the inflatable proximal and distal sections have a lower porosity than the sections of the first layer located at the proximal and distal skirt sections.

17. The balloon catheter of claim 16 wherein the section of the first layer located at the inflatable proximal and distal sections each have a porosity about 10 to about 30% lower than the sections of the first layer located at the proximal and distal skirt sections.

18. The balloon catheter of claim 1 wherein the first layer of the balloon is formed of a material selected from the group consisting of expanded polytetrafluoroethylene, ultra high molecular weight polyolefin, porous polyolefin, and porous polyurethane.

19. The balloon catheter of claim 18 wherein the balloon includes a second layer formed of an elastomeric material, which extends from the proximal skirt section to the distal skirt section, and which is secured to the first layer.

20. A balloon catheter, comprising:
   a) an elongated shaft having a proximal end, a distal end, and at least a first lumen; and
   b) a balloon on a distal shaft section, having an interior in fluid communication with the first lumen, a proximal end, a distal end, and at least a first layer formed of expanded polytetrafluoroethylene, the first layer in a noninflated configuration having an inflatable central section between the proximal and distal ends of the balloon with a longitudinal compaction of about 10% to about 60%, an inflatable proximal section proximal to the central section with a longitudinal compaction less than the first layer inflatable central section and which inflates to a tapered configuration, an inflatable distal section distal to the central section with a longitudinal compaction less than the first layer inflatable central section and which inflates to a tapered configuration, a proximal skirt section secured to the shaft, and a distal skirt section secured to the shaft.

21. The balloon catheter of claim 20 wherein the longitudinal compaction of the inflatable proximal section and the inflatable distal section of the first layer is about 10% to about 40%.

22. The balloon catheter of claim 20 wherein the inflatable central section of the first layer has a longitudinal compaction of about 30% to about 50%, and the inflatable proximal and distal sections each have a longitudinal compaction of about 10% to about 20%, and the proximal and distal skirt sections each are not longitudinally compacted.

23. An expandable tubular medical device or component, comprising a tubular body having a proximal end, a distal end, a length extending from the proximal to the distal end, and having at least a first layer formed of a porous polymeric material with a first section, and with a second section longitudinally adjacent to the first section and extending at least in part along a central portion of the length of the tubular body, the second section being longitudinally compacted by more than the first section, so that in a nonexpanded configuration prior to expansion of the tubular body the second section has a lower porosity than the first section.

* * * * *